United States Patent [19]

Joy et al.

[11] 4,274,162

[45] Jun. 23, 1981

[54] ARTIFICIAL REPLACEMENT FOR A LARYNX

[76] Inventors: Michael Joy, 118 Burnhamthorpe Rd., Islington, Ontario; Richard E. Moon, 100 Wellesley St. E., Apt. 1013, Toronto, Ontario; Abul Quashem, 93 Hanson Rd., Mississauga, Ontario; Alex Lo, 89 Wilcock St., Toronto, Ontario; Vijay S. Dayal, 12 Harper Ave., Toronto, Ontario, all of Canada

[21] Appl. No.: 41,960

[22] Filed: May 23, 1979

[51] Int. Cl.³ .............................................. A61F 1/20
[52] U.S. Cl. ............................................................. 3/1.3
[58] Field of Search ............................................... 3/1.3

[56] References Cited

U.S. PATENT DOCUMENTS

| 2,804,076 | 8/1957 | Giraudon | 3/1.3 UX |
| 3,747,127 | 7/1973 | Taub | 3/1.3 |
| 4,044,402 | 8/1977 | Edwards | 3/1.3 |

FOREIGN PATENT DOCUMENTS

| 1248230 | 8/1967 | Fed. Rep. of Germany | 3/1.3 |
| 469470 | 8/1977 | U.S.S.R. | 3/1.3 |

*Primary Examiner*—Clifford D. Crowder
*Attorney, Agent, or Firm*—Hirons, Rogers & Scott

[57] ABSTRACT

A larynx replacement for installation in a patient's trachea comprises an air passage controlled by a valve. The valve is gas operated and sensing means are provided for detecting the presence of food or liquid in the patient's throat to close the valve, and in this way to prevent the passage of food or liquid beyond the replacement larynx.

10 Claims, 5 Drawing Figures

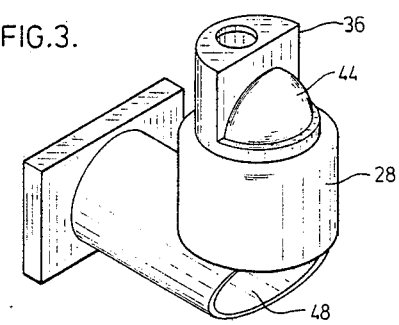
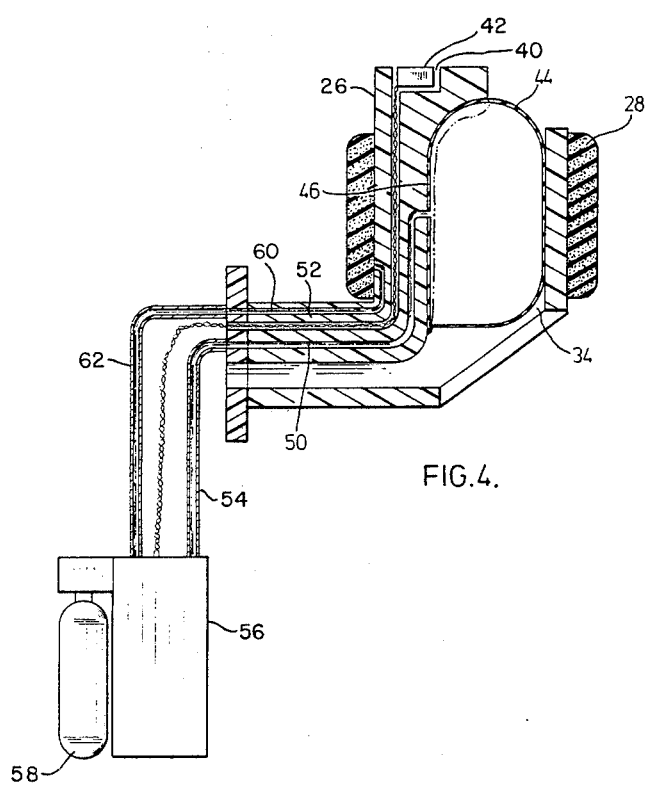

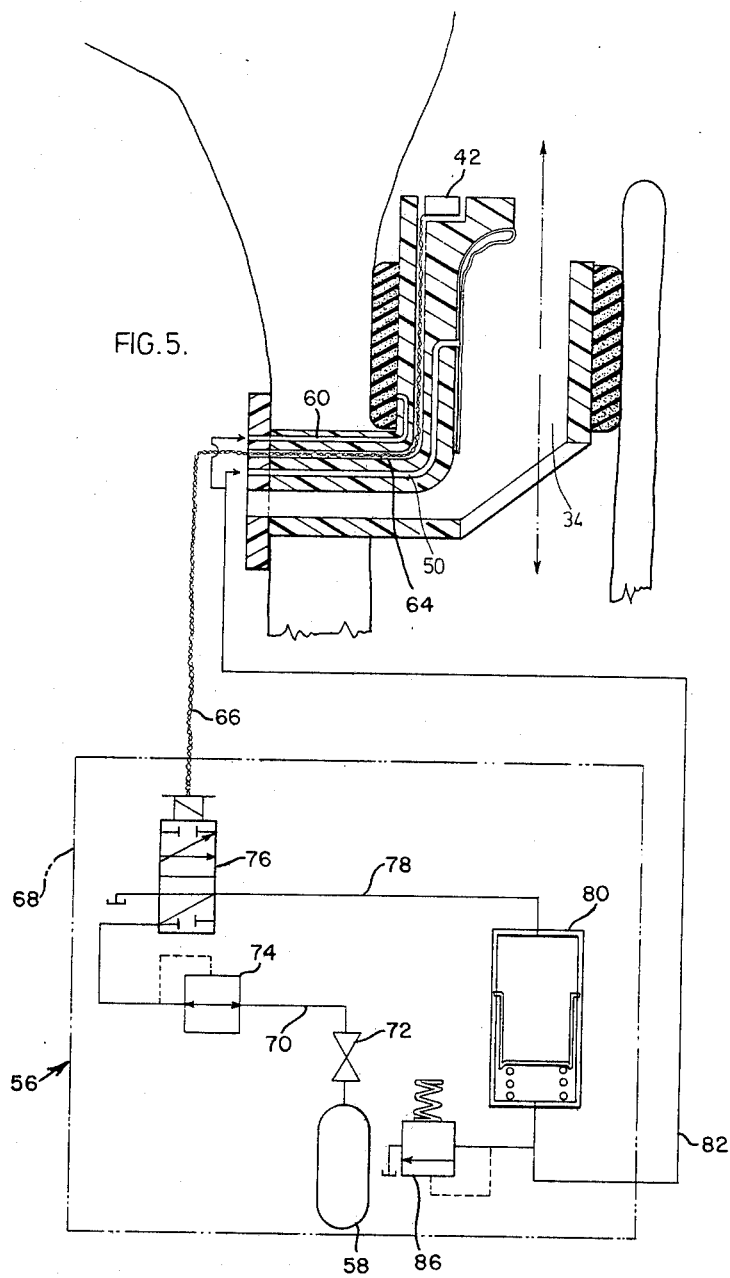

ARTIFICIAL REPLACEMENT FOR A LARYNX

FIELD OF THE INVENTION

This invention relates to the field of surgical operation conducted on the throat, and more particularly to an artificial replacement for the larynx.

BACKGROUND OF THE INVENTION

The arrest of throat cancer in human patients frequently involves the surgical removal of the patient's larynx. The larynx constitutes the human voice box, and consists of several cartilages and membranes. It contains the vocal cords, the tension or position of which changes so that air which passes from the lungs to the mouth via the larynx can be made to produce different sounds of the voice. Another function of the larynx is to prevent food and liquids from entering the trachea, or wind pipe, during the act of swallowing. Located adjacent to and immediately behind the trachea, in the human throat, is the food pipe or esophagus, and both the trachea and the esophagus, of course, communicate with the mouth.

DESCRIPTION OF THE PRIOR ART

Operations for total removal of the larynx leave the patient with an opening from the neck into the trachea, through which the patient breathes, and no connection for air passage to the trachea from the nose or mouth. Whilst this provides full protection against food and liquid entry into the trachea, it leaves the patient with no effective voice. Many patients who have experienced this operation are able to learn the technique of esophageal speech, in which air is swallowed into the esophagus and subsequently regurgitated back into the mouth, causing vibration of the tissues of the hypopharynx (lower part of the throat), producing a sound. About a third of patients are unable to learn this technique. Only a third of patients are able to produce a satisfactory voice; even in these satisfactory cases the voice is considerably less intelligible than the normal voice.

In another version of the operation, it is known to leave a small fistula or opening from the trachea upwardly into the mouth, as well as creating the opening in the throat to the trachea, when the larynx is removed. This provides the patient with improved voice capabilities, since the patient can partially use the mouth to produce sounds from exhaled air, but exposes the patient dangerously to aspiration pneumonia as a result of food and water entering the trachea.

In patients who cannot produce a voice in any other way, "external electrolarynxes" are available. These are devices which are held by hand against the exterior of the neck. When activated by push button a vibration is produced, which passes to some extent through the neck tissues into the pharynx and mouth. The vibrations can be articulated by the lips and tongue producing a sort of voice. This type of device produces a less satisfactory voice than the former two methods. Furthermore it is clumsy, requiring hand operation.

SUMMARY OF THE INVENTION

It is an object of the present invention to provide a novel larynx replacement.

It is a further object of the present invention to provide a removable larynx replacement for insertion in the patient's throat which effectively prevents food and water from entering the trachea, whilst allowing exhalation through the mouth and nose of the patient.

The present invention provides an artificial larynx which may be installed in the trachea of the patient following surgery. It has a passageway extending therethrough, to form a part of the patient's trachea, but is provided with a valve means which can close the trachea selectively to prevent food, liquid, etc. entering the trachea. Sensing means are provided which sense the presence of food or liquid in the patient's throat, to sense the pressure exerted by a moving bolus of food and cause closing of the valve to close the trachea during swallowing. A transverse passage below the valve communicates with air outside the patient's neck, to permit breathing in an emergency, if the valve becomes blocked. The device is easily inserted and removed, and is fully washable.

Thus according to the present invention, there is provided a larynx replacement for installation in a patient's trachea, and comprising:

a sleeve adapted for insertion into the trachea to extend along the axis of length thereof, the exterior of said sleeve being adapted to fit in substantially airtight manner against the interior walls of the trachea;

a passageway extending lengthwise through said sleeve, so as to form a part of the trachea after installation of the sleeve therein;

a valve operable to open and close said passageway;

sensing means located at the upper part of said sleeve, about the valve, and operatively connected to cause movement of the valve in response to conditions sensed by said sensing means;

a conduit extending transversely of said sleeve and providing air communication between the trachea, at a point below the valve, and the exterior of a patient's neck after installation of said larynx replacement therein.

Such a larynx replacement in many respects imitates the function of the natural larynx. It controls the opening and closing of the trachea in response to the presence or absence of food and drink for swallowing. External control means are provided, e.g. to be worn by the patient and connected to the sensing means, providing operating power and control for opening and closing of the valve as required. The transversely extending conduit insures that the patient can continue breathing whilst the valve is closed or blocked. This latter feature will only be used in an emergency. In addition, however, normal exhalation of air can take place through the larynx replacement and thence through the patient's mouth. This allows improved voice projection by the patient, since he can use mouth, tongue, lips, etc. to form sounds. This is a significant improvement over the situation where the patient breathes continuously through a hole in the neck, and must form sounds in the body on exhalation, as a voice. In particular, longer vocal phrases than in esophageal speech are possible, and superior consonant sounds are facilitated. The larynx replacement of the present invention also provides for the possibility of inclusion of artificial vocal cords in the body of the apparatus in order to produce the sounds necessary for speech.

DESCRIPTION OF THE PREFERRED EMBODIMENTS

In the preferred embodiment according to the present invention, the valve is a resilient, substantially liquid impermeable membrane, resiliently movable between a first position in which the membrane lies against one wall of the sleeve, to leave the passageway through the trachea open, and a second position in which it extends between opposed walls of the sleeve to close the passageway. There is preferably supplied a source of pneumatic pressure, e.g. a cylinder containing pressurized carbon dioxide, externally of the device, and adapted to move the valve membrane in response to signals received from the sensing means. Preferably also, the sleeve member comprises a radially expansible cuff, e.g. of polyurethane foam, connected to a source of pneumatic pressure such as a pressurized carbon dioxide cylinder which causes the sleeve to expand and come into airtight contact with the walls of the trachea, to prevent solid or liquid matter passing down the trachea around the outside of the sleeve, and to keep the sleeve properly positioned within the trachea.

The sensing means suitably comprises a transistor susceptible to pressure and touch, connected to suitable logic and time circuits to control the supply of pneumatic pressure from a pressurized gas cylinder as aforesaid, to open and close the valve. Thus where the device is pneumatically operated there is desirably an external power pack, including suitable logic and timing circuits connected to the sensing means, and a series of valves, to be operated by the logic and timing circuits, to allow pressurization of the membrane and the cuff of the sleeve by pressurized carbon dioxide provided in the gas cylinder.

The transistor may conveniently be a pressure transistor as for example a silicon NPN planar transistor of which the emitter-base junction is mechanically coupled to a diaphragm. A pressure differential applied to the diaphragm, as for example resulting from increased air pressure or touch, produces a large, reversible change in the transistor gain. A typical transistor of value in the present invention is available from Stow Laboratories Inc. of Hudson, Mass. and is identified by that company by the trade mark PITRAN. Most desirably, the patient himself can readily remove and replace the artificial larynx, as conditions dictate.

BRIEF REFERENCE TO THE DRAWINGS

A specific embodiment of the present invention is illustrated in the accompanying drawings in which:

FIGS. 2 and 3 are perspective views of the larynx replacement of FIG. 1;

FIG. 4 is a diagrammatic vertical cross section through the apparatus of FIG. 2 and FIG. 3, and showing diagrammatically its connection to an external power pack;

FIG. 5 is a circuit diagram illustrating the control and operation of the apparatus of FIGS. 1-4, shown in cross section thereon.

In the drawings, like reference numerals indicate like parts.

DETAILED DESCRIPTION OF THE SPECIFIC PREFERRED EMBODIMENT

Figure 1:
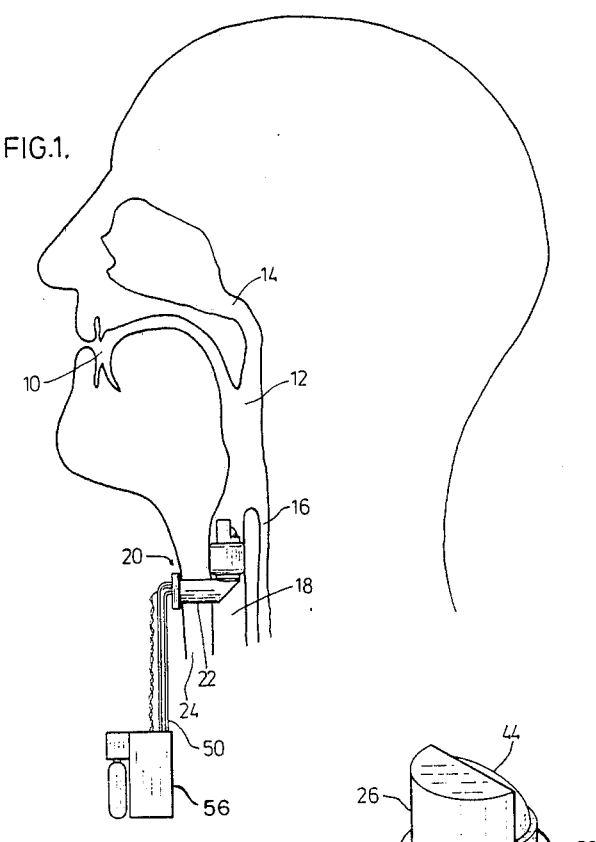
FIG. 1 is a diagrammatic sagittal cross section of the mouth and throat portion of a patient, with a larynx replacement according to the present invention installed therein.

With reference to FIG. 1, numeral 10 denotes the patient's mouth, from which extends downwardly the throat 12. The nasal passages 14 extend upwardly from the throat 12. Lower down, the throat divides into the food pipe or esophagus 16 and the windpipe or trachea 18, which is located forwardly of the esophagus 16. Normally, in the healthy patient, the epiglottis is located at the location of the division of the throat, the depiglottis being the upper cartilage of the larynx, which is itself located at the top of the trachea 18. As illustrated, however, the natural larynx has been surgically removed and replaced by an artificial replacement larynx 20 in accordance with the present invention. The artificial larynx 20 is installed and projects through an aperture 22 surgically formed in the exterior wall 24 of the patient's neck, and into the top part of the trachea 18.

The artificial larynx 20 is generally L-shaped as viewed in side elevation, having an upright sleeve 26 with a cylindrical outer expansible cuff 28, and a transverse conduit 30. The forward extremity of the transverse conduit 30 has a generally rectangular enlarged front flange plate 32. As shown in FIG. 1, the artificial larynx 20 is installed with the transverse conduit 30 thereof in the aperture 22 in the neck, and the flange plate 32 against the exterior of the neck wall 24. Cuff 28 is of open cell foam structure, is resilient and formed of a biocompatible material, and is pressurizable to be a resiliently tight fit in the trachea 18 to prevent passage of fluid through the trachea 18 outside of the cuff 28, by means described hereinafter.

Figure 2:
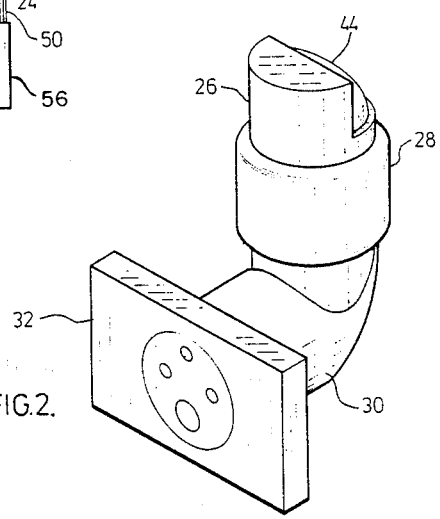

The upright sleeve 26 is cylindrical in general form, and has a passageway 34 extending longitudinally therethrough, so that after installation the passageway 34 forms a part of the trachea 18. The upper part of upright sleeve 26, above the cuff 28, is cut away to form a semi-cylindrical top portion 36. This top portion is solid, with its top wall recessed at 40 (FIG. 4) to receive therein a pressure responsive transistor 42, exposed to the throat 12 where the device is installed. A valve means in the form of a flexible inflatable balloon 44 is provided, seated against the inner front wall 46 of the passageway 34. When non-inflated, the balloon 44 sits against the inner front wall 46, in the position shown in broken lines in FIG. 4 and in full lines in FIG. 5. In this condition free communication is provided through passageway 34 and lower opening 48 therefrom, between the throat 12 and the trachea 18. When the balloon 44 is pressurized and inflated, however, it expands to close the passageway 34, in the position shown in FIGS. 2 and 3, and in full lines in FIG. 4.

In order to inflate and pressurize balloon 44 so as to close passageway 34, a bore 50 is provided, extending from the front of the artificial larynx 20, through the flange 32 and upper wall 52 of transverse conduit 30, through the front wall 46 of the passageway 34 and into the interior of the balloon 44. Exteriorly of flange 32, bore 50 connects by means of tube 54 to exterior control unit 56, in which it is connected by various control devices, described below, to a source of pneumatic pressure, namely a small carbon dioxide cylinder 58. A second bore 60 is provided in the upper wall 52 of the transverse conduit 30, extending from the exterior of the flange 32 and communicating with the interior of the cuff 28 of upright sleeve 26. Exteriorly of flange 32, second bore 60 connects by means of tube 62 to control unit 56, and thence to pneumatic pressure cylinder 58. A third bore 64 extends through flange 32, upper wall 52 of transverse conduit 30 and front wall 46 thereof, for passage of electrical wire 66 to connect transverse 42 in top recess 40 with exterior control unit 56.

When the artificial larynx replacement 20 is inserted into the position in the patient as shown in FIGS. 1 and 5, pneumatic pressure is applied from cylinder 58 by appropriate control means to cuff 28, so that cuff 28 expands and comes into sealing engagement with the inner walls of the trachea 18. Now, the only communication from the patient's throat 12 to the trachea 18 is through the passageway 34, so that valve member or balloon 44 provides complete control of passage of material into the trachea 18. This control of the inflation and deflation of the balloon 44 is accomplished by means of the pneumatic cylinder 58, communicating through bore 50 through suitable control means, so that balloon 44 expands and contracts very rapidly, providing substantially instantaneous control over passageway 34. The inflation is accomplished in response to signals received from transistor 42, which is sensitive to changes in pressure occuring in the throat 12 of the patient, e.g. by the presence of food therein, and by the reaction of muscles and nerves in the throat region preparatory to swallowing. As the patient prepares to swallow, the transistor 42 detects the change in pressure in the throat 12 caused thereby, and the signals transmitted to the exterior control 56 and pressure cylinder 58 cause instantaneous inflation of the balloon 44 to close the passageway 34. The transistor 42 is also sensitive to touch, so that, in the event that any food or liquid particles pass into contact with the transistor 42, it immediately causes closing of the passageway 34 by operation of balloon valve 44. When the passageway 34 is thus closed by the balloon valve 44, the patient may still breathe by the passage of air from outside the neck, through transverse conduit 30 below the valve member 44 and into the trachea. This breathing can continue as long as the valve balloon 44 is closed. Exhalation of air from the lungs, when the valve 44 is open, will be primarily through the passageway 34 and through the patient's mouth, allowing for the production of sounds by use of tongue and lips. In the event of emergencies, the patient can himself remove the entire artificial larynx replacement 20 through the surgical aperture 22 in the patient's neck, to the exterior of the body. It will be appreciated that the artificial larynx 20 is placed in position and retained therein by its close fit in the desired location and by the pressurized expanded cuff 28, but is not otherwise secured, thereby permitting its withdrawal in emergencies, for example if passageway 34 and/or conduit 30 should become plugged.

Thus the device according to the present invention creates a wide fistula between the trachea 18 and the pharynx or throat 12, which allows free flow of air to pass through the mouth and nose and allow the production of consonant sounds whilst leaving the sense of smell intact. Aspiration of food into the trachea is prevented by the small, easily removable device according to the invention, which sits in the opening between the trachea and the pharynx and closes on contact with food or in response to pressure changes in the pharynx caused by imminent swallowing. Leakage around the device is prevented by the cushion-like cuff 28, made of biologically inert material. Contact sensing is made with the small pressure sensitive transistor 42. The electronic circuit, batteries and pneumatic power pack are contained in a small plastic container which may be carried on the person's belt. A pair of small, vibrating membranes designed to imitate the human vocal chords may if desired be provided, in the passageway 34 below the valve membrane 44. The patient may initiate coughing, as required, by manually closing the valve 44 by means of a push button provided on the control unit, breathing out hard against the closed valve, and then allowing the valve to open. The high velocity air stream will carry debris out of the trachea. During sleep, when the active valve is not required, the larynx replacement 20 according to the invention can be removed and the patient can breathe through a tracheostomy.

FIG. 5 shows diagrammatically the pneumatic portion of the external control unit 56 and its mode of operation. The control unit 56 includes a housing 68, within which is located the small carbon dioxide cylinder 58 referred to above. The outlet for pneumatic pressure on the cylinder 58 is via outlet line 70 in which is interposed a needle valve 72, to a pressure regulator 74 of known type. The transistor 42 in the unit 20 is electrically connected by wires 66 to an electro-pneumatic valve 76. The outlet from valve 76 is connected to pneumatic pressure line 78 and thence to a pneumatic actuator in the form of a rolling diaphragm cylinder 80. The pneumatic output tube 82 from the downstream side of the diaphragm cylinder 80 connects both to the bore 50 communicating with the interior of the balloon valve 44, and with the second bore 60, communicating with the interior of the expandable cuff 28. The pneumatic output tube 82 also has a branch 84 communicating, within the housing, with a pressure relief valve 86, set to open at pre-set maximum pressure, to prevent excessive pneumatic pressures being communicated to the device 20. All of the components of the external control unit, namely the carbon dioxide cylinder 58, needle valve 72, pressure regulator 74, electro-pneumatic valve 76, rolling diaphragm cylinder 80 and pressure relief valve 86, are located within the housing 68 to provide compact external control unit, capable of being worn on the clothing of the operator e.g. hooked on a belt.

The operation of the device will be clear from the above description and diagrammatic drawings. When the transistor 42 senses increase in pressure or touch, it produces through suitable electrical circuitry not shown a suitable signal to open the electro-pneumatic valve 76, so as to pressurize the rolling diaphragm cylinder 80 from the small carbon dioxide cylinder 58. Then, pneumatic pressure up to a predetermined level as set by pressure relief valve 86 is supplied through tube 82, to expand the cuff 28 and make it a tight, substantially fluid impervious fit against the walls of the trachea, and also to close the valve 44. This takes place substantially instantaneously, the balloon valve 44 being very flexible although air impermeable, and having natural rest positions either against the passageway front wall 46 of the device 20, or against the full circumferential inner surface of the passageway 34, i.e. it will "flip-flop" between these two positions in response to pneumatic pressure, very rapidly. No significant time interval is required to inflate the balloon 44 into its closed position. When the signal from transistor 42 is terminated, the electro-pneumatic valve 76 closes, so that the diaphragm of the rolling diaphragm cylinder 80 is no longer pressurized from the upstream side. The elastic resilience of the balloon 44 and cuff 28 causes back flow of pneumatic pressure into the downstream side of the rolling diaphragm cylinder 80, which permits relaxation thereof, so that the membrane or balloon 44 flips to its open position as shown in FIG. 5 substantially instantaneously, and the cuff becomes depressurized. Then, whilst the device 20 is held loosely in position as shown, it can readily be removed by the patient when required.

The airtight seal caused by inflating cuff 28 is only necessary when transistor 42 senses touch or increased pressure, so as to prevent the passage of foods or liquids into the esophagus 16.

The individual components of the external control unit 56, namely the small carbon dioxide cylinder 58 and its associated needle outlet valve 72, the pressure regulator 74, the electro-pneumatic valve 76, the rolling diaphragm cylinder 80 and the pressure relief valve 86, are all known, standard pieces of equipment, available commercially on the market, and do not therefore require description in detail herein. The use of a rolling diaphragm cylinder as the pneumatic actuator 80 has particular advantages in the device according to the invention, since it provides substantially immediate surges of pressure from the electro-pneumatic valve to the balloon valve 44 and cuff 28, in response to electronic triggering by transistor 42, whilst at the same time it allows substantially instantaneous relaxation of the formerly pressurized items, back to their open position, once the pressurization from electro-pneumatic valve 78 is released.

We claim:

1. A larynx replacement for installation in a patient's trachea, and comprising:
   a sleeve adapted for surgical insertion into the trachea to extend along the axis of length thereof, the exterior of said sleeve being adapted to fit in substantially airtight manner against the interior walls of the trachea;
   a passageway extending lengthwise through said sleeve, so as to form a part of the trachea after installation of the sleeve therein;
   a valve operable to open and close said passageway;
   sensing means located at the upper part of said sleeve, above the valve, and operatively connected to cause movement of the valve in response to conditions sensed by said sensing means;
   a conduit extending transversely of said sleeve and providing air communication between the trachea, at a point below the valve, and the exterior of a patient's neck after surgical installation of said larynx replacement therein.

2. The larynx replacement of claim 1 wherein said sensing means senses conditions in the region of the pharynx above the larynx replacement, and operates to close said valve upon sensing the presence of food or liquid in said region.

3. The larynx replacement of claim 2 wherein said valve is a resilient, substantially liquid impermeable membrane, resiliently movable between a first position in which the membrane lies against one wall of said sleeve to open said passageway, and a second position in which it extends across between opposed walls of said sleeve to close said passageway.

4. The larynx replacement of claim 3 wherein the sensing means is a pressure and touch sensitive transistor adapted to produce an electrical signal upon sensing pressure changes or upon being contacted by solids or liquids in the pharynx, the electrical signal so produced being operative to cause closing of the membrane valve.

5. The larynx replacement of claim 4 wherein the resilient membrane valve is movable from its first position to its second position in response to penumatic pressure supplied to the membrane, and resiliently retractable to its first position upon discontinuence of supply of said pneumatic pressure, the electrical signal from said transistor causing supply of pneumatic pressure to the membrane.

6. The larynx replacement of claim 5 including a control unit having a source of pneumatic pressure and an electro-pneumatic valve electrically connected to the transistor and interposed in the pneumatic connection between the pneumatic pressure source and the membrane, the electro-pneumatic valve being operated by signals from the transistor to supply pneumatic pressure to the membrane valve.

7. The larynx replacement of claim 6 wherein the control unit further includes a pneumatic actuator, in the form of a rolling diaphragm cylinder, adapted to transmit changes in pneumatic pressure from the electro-pneumatic valve to the membrane valve.

8. The larynx replacement of claim 7 wherein the sleeve includes a radially outer annular cuff of resilient material, said cuff being resiliently expandable to form a substantially air tight contact with the inner wall of the trachea.

9. The larynx replacement of claim 8 wherein the cuff is resiliently expandable in response to pneumatic pressure so supplied thereto.

10. The larynx replacement of claim 9 wherein the cuff is pneumatically connected to the pneumatic actuator, so as to be pneumatically pressurized and depressurized in response to signals from the transistor, along with the membrane valve.

* * * * *